United States Patent [19]

Tymonko

[11] Patent Number: 4,822,401
[45] Date of Patent: Apr. 18, 1989

[54] SAFENING OF HERBICIDAL CLOMAZONE APPLICATIONS WITH ORGANOPHOSPHORUS COMPOUNDS

[75] Inventor: John M. Tymonko, Hamilton Square, N.J.

[73] Assignee: FMC Corporation, Philadelphia, Pa.

[21] Appl. No.: 141,016

[22] Filed: Jan. 5, 1988

[51] Int. Cl.$^4$ .................. A01N 57/04; A01N 43/80
[52] U.S. Cl. ........................................... 71/87; 71/86; 71/88
[58] Field of Search ........................... 71/87, 88

[56] References Cited

U.S. PATENT DOCUMENTS

| | | | |
|---|---|---|---|
| 2,571,989 | 10/1951 | Schrader | 558/183 |
| 2,970,080 | 1/1961 | Oros et al. | 514/119 |
| 4,379,716 | 4/1983 | Schafer et al. | 71/87 |
| 4,405,357 | 9/1983 | Chang | 71/88 |
| 4,507,143 | 3/1985 | Schafer et al. | 71/87 |
| 4,605,431 | 8/1986 | Schafer et al. | 71/87 |
| 4,692,182 | 9/1987 | Chang | 71/88 |

OTHER PUBLICATIONS

Parker, C., "Herbicide Antidotes-A Review", Pesticide Science, 14, pp. 40–48, 1983.
*Pesticide Manual*, 5th Ed., pp. 236, 199, 418, 222, 496.
Arle, "trifluralin—Systemic Insecticide Interactions on Seedling Cotton".
Hassawy, Hamilton, "Effects of Trifluralin and Organophosphorus Compounds on Cotton Seedlings".
*Pesticide Manual*, 7th Ed., pp. 205, 410.

*Primary Examiner*—Richard L. Raymond
*Assistant Examiner*—Susan P. Treanor
*Attorney, Agent, or Firm*—Patrick C. Baker; H. Robinson Ertelt

[57] ABSTRACT

The spectrum of crops which can be protected against weeds by clomazone is widened to include cotton, corn, wheat, oats, barley, sorghum and others, by combining the clomazone treatment with application of antidotal amounts of an organophosphorus pesticide of the formula

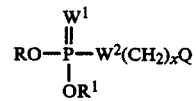

wherein $W^1$ and $W^2$ independently are oxygen or sulfur, x is an integer of from 1 to 4, Q is $SR^2$ or

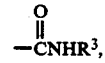

and R, $R^1$, $R^2$ and $R^3$ are alkyl($C_1$-$C_{13}$), provided that when Q is $SR^2$, both $W^1$ and $W^2$ are not oxygen.

The organophosphorus compounds include phorate, disulfoton, terbufos, demeton and dimethoate.

33 Claims, No Drawings

SAFENING OF HERBICIDAL CLOMAZONE APPLICATIONS WITH ORGANOPHOSPHORUS COMPOUNDS

TECHNICAL FIELD

This invention relates to the control of undesirable vegetation encountered in the cultivation of various plant species, particularly agronomic crops.

BACKGROUND OF THE INVENTION

The compound 2-[(2-chlorophenyl)methyl]-4,4-dimethyl-3-isoxazolidinone, hereinafter referred to by the common name "clomazone", is a potent herbicide as evidenced by its ability to control, for full growing seasons and at low application rates in soybean stands, a broad spectrum of grasses and broadleaf weeds that compete with soybeans. However, clomazone is phytotoxic to other crops when applied at rates effective to control undesired vegetation, such contact resulting from drift to adjacent fields planted with low tolerance crops or from carryover when soybean fields treated with clomazone are rotated to a crop sensitive to clomazone. Typical of the crops sensitive to herbicidal rates of application of clomazone are cotton, wheat, corn and barley.

Although clomazone can be, and is, sold with suitable instructions to prevent exposure to sensitive crops, it will be evident that measures that will increase the tolerance of desirable plants to clomazone without substantial diminution of herbicidal efficacy against weeds, will greatly expand the usefulness of clomazone and ultimately result in lower cost.

In this specification the term "crops" includes not only agronomic crops but plants of all kinds, particularly cereal and non-cereal grassy crops, such as corn, wheat, oats, barley, rice, cotton, sorghum, sugar cane, sugar beets and peanuts, including hybrids thereof.

SUMMARY OF THE INVENTION

It has now been found, in one aspect of the invention, that by combining clomazone treatment and treatment with one or more organophosphorus compounds of formula I below, clomazone may be applied with effective weed control to crops heretofore damaged by clomazone, The discovery thereby opens up applicability of clomazone to control of weeds in crops in addition to soybeans and elminates or substantially diminishes the risk of injury to the crops by drift of clomazone to fields adjacent to a soybeans stand or by rotation of a clomazone-treated soybeans field to another crop.

In another aspect of the invention, certain organophosphorus pesticidal compounds are combined with clomazone either by admixture prior to application, or by separate application. The combined application not only safens the crops against phytotoxic effects of clomazone but also combats insects and other pests to which the crops may be subject.

DETAILED DESCRIPTION

Clomazone is described in U.S. Pat. No. 4,405,357 issued Sept. 30, 1983 to J. H. Chang, specifically Example 16 thereof.

The organophosphorus pesticidal compounds found useful as safeners or antidotes for clomazone are those of the formula (I):

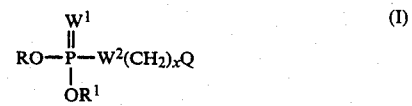

wherein $W^1$ and $W^2$ independently are oxygen or sulfur, x is an integer of from 1 to 4, preferably 1 or 2, Q is $SR^2$ or

and R, $R^1$, $R^2$ and $R^3$ are alkyl, provided that when Q is $SR^2$, both of $W^1$ and $W^2$ are not oxygen. Alkyl may be straight chain or branched and may contain any number of carbon atoms, such as 1 to 13 or more. Preferably, alkyl is lower alkyl ($C_1$–$C_6$) such as methyl, ethyl, n- and isopropyl, n-butyl, t-butyl, etc. The number of carbon atoms in R, $R^1$, $R^2$ and $R^3$ may be the same or different.

When Q is $SR^2$ the compounds include phosphorodithioates such as O,O-diethyl S-ethylthiomethyl phosphorodithioate (common name "phorate"), O,O-diethyl S-2-ethylthioethyl phosphorodithioate (common name "disulfoton") and S-tert-butylthiomethyl O,O-diethyl phosphorodithioate (common name "terbufos"), or a mixture of isomers such as a 65:35 mixture of O,O-diethyl O-2-ethylthioethyl phosphorothioate (common name "demeton-O") and O,O-diethyl S-2-ethylthioethyl phosphorothioate (common name "demeton-S"). The isomeric mixture has the common name "demeton." The isomers have been separated and are useful in the invention singly or in admixture.

When Q is

the compounds of formula I include O,O-dimethyl S-methylcarbamoylmethyl phosphorodithioate (common name "dimethoate") and O,O-dimethyl S-methyl-carbamoylmethyl phosphorthioate (common name "omethoate").

The foregoing and other compounds of formula I are known as evident from U.S. Pat. Nos. 2,494,283, 2,571,989, 2,586,655, 2,596,076, 2,970,080, 2,759,010 and the patents and literature cited in The Pesticide Manual (7th Edition). Related organophosphorus compounds are disclosed in U.S. Pat. Nos. 4,379,716, 4,507,143 and 4,605,431 as safeners for thiocarbamate herbicides such as triallate and diallate.

Clomazone and the organophosphorus safener are formulated and applied in accordance with procedures standard in herbicidal treatments as modified by the labels established for each of the active ingredients. Generally, the herbicides and the safener are applied in dilute form with an agriculturally acceptable, relatively inert, solid or liquid carrier to the locus where herbicidal effect and safening are needed. Since, as is well known, the formulation and mode of application of an agricultural chemical may affect activity in a given application; the herbicide and safener may be formulated separately or in admixture as emulsifiable concentrates (EC's), as granules preferably of relatively large particle size, as wettable powders, as solutions or suspensions, or in other forms. Preferably, the organophosphorus safener is applied prior to application of the clomazone, typically in a premergent, postemergent or pre-plant incorporated manner, alone or as a tank mix with other pesticides and/or with clomazone. The safener may also be applied to seeds of crops prior to or simultaneously with planting.

To obtain the benefits of the invention, the amount of the organophosphorus safener will be in excess of the amount of clomazone, on the order of two to three times by weight as much, or more, of the safener as clomazone. Optimum ratios are routinely determined for the particular crop and organophosphorus safener selected for treatment with clomazone. Generally, the ratio of safener to clomazone should be at least about 2:1 by weight but may range as high as about 10:1 by weight or more. Keeping in mind such ratios, clomazone and the safener may be formulated singly or in admixture to contain between about 0.01% and 95% by weight active ingredient, the balance being a carrier (one or more) together, in some formulations, with a surface active agent. Typically, the carrier will comprise about 4–98% by weight of the formulation and surface active agent about 1–15% by weight.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as zylene, heavy aromatic naphthas, isophorone and other non-volatile organic solvents. For example, a useful emulsifiable concentrate formulation, designated "4EC" because it contains four pounds of active ingredient per gallon of concentrate (0.479 kg/liter), contains 53.01 parts of clomazone and/or safener, 6.0 parts of a blend of alkyl-naphthalenesulfonate and polyoxyethylene ethers and emulsifiers, 1.0 part of epoxidized soybean oil as stabilizer, and as solvent 39.99 parts of petroleum distillate having a high flashpoint.

Granular formulations are particularly useful for aerial distribution. Useful granular formulations may be of several types. Impregnated granules are those wherein the active ingredient is applied to large particles of an absorbent carrier, such as an attapulgite or kaolin clay, corncobs, expanded mica, normally in the form of a solution in a solvent. Surface-coated granules may be produced by spraying the molten active ingredient onto the surface of a generally nonabsorbent particle or by spraying on a solution of active ingredient in a solvent. The core may be water-soluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders, as by compaction rollers, by extrusion through a die or by use of a granulating disc. Granular formulations may vary widely in concentration, with useful formulations containing as little as 0.5% or as much as 95% of active ingredient.

Wettable powders are in the form of finely divided particles which disperse readily in water or other dispersant. The wettable powder is ultimately applied to the soil as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations and in the compositions of the invention include, for example, the alkyl and alkylaryl sulfonates and sulfates and their sodium salts; polyethylene oxides; sulfonated oils, fatty acid esters of polyhydric alcohols; and other types of surface active agents, many of which are available in commerce.

As indicated, the formulations may be applied without further dilution or as dilute solutions, emulsions or suspensions in water or other suitable diluent. The compositions may be applied to the area wherein control is desired, prior to or after emergence in the case of agronomic crops, by spraying onto the surface of the soil in the case of liquid compositions or by distribution from mechanical equipment in the case of solids.

It may be preferable to blend the safener and/or the clomazone formulation into the upper layer of soil by cultivation or to apply the safener to seeds of the crop to be protected. Safening amounts for application to seed will vary according to the plant to be protected, soil conditions, and the rate of application of clomazone. For corn seed, about 0.05% to 1.5% by weight, preferably about 0.1% to 0.5% by weight, on weight of seed is effective.

The active compounds of the invention may be formulated and/or applied with insecticides, fungicides, nematicides, plant growth regulators, fertilizers, and other agricultural chemicals. In applying the active compounds of this invention, whether formulated alone or with other agricultural chemicals, an effective amount of each active ingredient is employed. The amount constituting an effective amount is variable, depending on the ratio of safener to clomazone and other factors such as the type of soil, the expected pattern of rainfall or irrigation, the plant species to be controlled, and the crop, if any, to be grown. Generally, a uniform application of from about 0.01 to about 0.5 kilograms per hectare of clomazone will be employed, more preferably, from 0.06 to 0.4 kilograms per hectare. The organophosphorus safener rate of application may range from about 0.04 to about 2.0 kilograms per hectare, more preferably about 0.3 to 1.5 kilograms per hectare. Generally, the rate of application of clomazone and safener in the field will be about 2 to 4 times that in the greenhouse.

HERBICIDAL EVALUATION

The herbicidal compositions and organophosphorus safeners of the invention were evaluated in a laboratory greenhouse as described below.

In conducting the following tests, technical materials were generally used as 1:1 acetone-water solutions containing 0.5% (V/V) of sorbitan monolaurate. Some tests, however, were conducted using a 4.0 pound/gallon emulsifiable concentrate (4 EC) formulation of clomazone. One test was conducted using a 1% wettable powder (1% WP) of phorate.

A typical 4 EC formulation is the following:

|  | % wt/wt |
| --- | --- |
| Clomazone (88.9% technical) | 52.40 |

-continued

|  | % wt/wt |
|---|---|
| Emulsifier A | 5.60 |
| Emulsifier B | 1.40 |
| Carrier/diluent | 40.60 |

Emulsifier A is a blend of the anionic calcium salt of dodecyl benzene sulfonate and a nonionic 30 molar ethylene oxide condensation product of nonylphenol. Emulsifier B is a nonionic paste of 100% polyalkylene glycol ether. The carrier/diluent is a refined xylene with a high flash point.

A typical 1% WP formulation is the following

|  | % wt/wt |
|---|---|
| Phorate (technical) | 1.00 |
| Base | 99.00 |
| 96.00% diluent | |
| 2.00% wetting/dispersing agent | |
| 2.00% dispersing agent | |

The wetting/dispersing agent is powdered sodium alkylnaphthalene sulfonate. The dispersing agent is highly purified sodium lignosulfonate.

1. Tolerance to Clomazone of Cereal Crops Treated with Certain Insecticides

A. Postemergence Test

Four disposable fiber flats (25 cm×15 cm×8 cm) for each rate of application of clomazone and each insecticide were filled to an approximate depth of 6.5 cm with a sterilized sandy loam soil. The soil was leveled and impressed with a template that provided five evenly spaced furrows in each flat that were 13 cm long and 0.5 cm deep. Seeds of spring and winter wheat (*Triticum aestivum*), barley (*Hordeum vulgare*), corn (*Zea mays*), and sorghum (*Sorghum vulgare*) were planted in the furrows of the flats. The five row template was again employed to firmly press the seeds into place. A topping soil prepared by mixing equal portions of sand and sandy loam soil was placed uniformly on top of each flat to a depth of approximately 0.5 cm. The flats were placed in a greenhouse where they were maintained for 7–8 days while the seeds germinated prior to spraying with insecticides.

The following amounts of technical organophosphorus insecticides were each weighed/pipetted into 125 mL Erlenmeyer flasks:

| Insecticide | Percent Active Ingredient | Actual Weight (g) | Rate of Application (kg/ha) |
|---|---|---|---|
| dimethoate | 95 | 0.1912 | 0.84 |
| demeton | 94.2 | 0.0648 | 0.28 |
| disulfoton | 95.4 | 0.2510 | 1.12 |
| terbufos | 99 | 0.2425 | 1.12 |
| phorate | 91.7 | 0.2634 | 1.12 |

Each insecticide was dissolved in 30 mL of acetone containing 0.5% (v/v) of sorbitan monolaurate. The volume of each was brought to 60 mL with water which also contained 0.5% sorbitan monolaurate.

The appropriate number of fiber flats containing the test plants described above were sprayed with the solutions of each insecticide via a machine sprayer calibrated to deliver 30 gallons/acre at 40 pound/sq. in. with the delivery nozzle located 27 cm above the plant canopy. The test flats were returned to the greenhouse where they were maintained for an additional 48–60 hours prior to spraying with clomazone.

From an emulsifiable concentrate formulation containing four pounds of clomazone per gallon of formulation (4.0 EC), 0.5624 gram was dissolved with mixing in 200 mL of distilled water. A 100 mL aliquot of this solution was removed and set aside for use as the 250 g/ha rate of application. The remaining 100 mL aliquot was diluted with an additional 100 mL of water. This 200 mL solution was mixed and divided into two 100 mL aliquots. One 100 mL aliquot was set aside for use as the 125 g/ha rate of application of clomazone. The second 100 mL aliquot was serially diluted as described above to provide the 63, 31, and 16 g/ha rates of application of clomazone.

The fiber flats previously sprayed with insecticide were now sprayed with each rate of application of clomazone via a machine sprayer calibrated to deliver 20 gallons/acre at 50 pounds/sq. in. with the delivery nozzle located 27 cm above the plant canopy. The test flats were again returned to the greenhouse where they were maintained for 10 days. Untreated control flats and flats treated with clomazone only were included in this test for comparison purposes. Following the 10 day exposure period each flat was evaluated for percent injury, i.e., discoloration or chlorosis, as compared to the untreated control. Using the percent injuries determined for the crops treated with insecticide and the percent injuries determined for those same crops not treated, the percent reduction of injury to the crops by treatment with insecticide for each rate of application of clomazone was calculated using the formula:

$$\text{Percent reduction of injury} = \frac{\text{Percent injury of unsafened crops} - \text{Percent injury of safened crops}}{\text{Percent injury of unsafened crops}} \times 100$$

(The foregoing method of determining injury and calculation were used in all subsequent tests described below).

As shown in Table 1 appended, the greatest reductions in clomazone injury to all the crops tested were provided by phorate, terbufos and disulfoton, and these three insecticides were approximately equal in their ability to reduce clomazone crop injury.

The small grains, wheat and barley, were best protected from the phytotoxic effects of clomazone by the treatments of insecticide. Corn and sorghum were less protected at the application rates tested.

B. Preemergence Test

This test was conducted similarly to the post-emergence test except that the soil surface in the fiber flats containing the planted seeds was sprayed with the solutions of the insecticides. The flats were placed in a greenhouse where they were maintained for seven days while the seeds germinated prior to spraying with clomazone. The test was evaluated ten days after spraying with clomazone.

The results of this preemergence test (Table 2 appended) were similar to those of the postemergence test. The greatest reduction in injury caused by clomazone resulted from the treatments of terbufos and phorate, which were nearly equal in their safening effect. Disulfoton also reduced crop injury, but was slightly less effective than terbufos and phorate.

As in the postemergence test the small grains were best protected by the treatments of insecticides. Corn and sorghum were safened but to a lesser extent.

2. Tolerance to Clomazone of Cotton and Cereal Crops Treated with Certain Insecticides: Pre-Plant Incorporated Test Sufficient amounts of technical insecticides for three replicates at each rate of application of clomazone were each weighed into the appropriate containers:

| Insecticide | Percent Active Ingredient | Amount Weighed in Grams for each Application Rate | | |
|---|---|---|---|---|
| | | 2.24 kg/ha | 1.12 kg/ha | 0.56 kg/ha |
| disulfoton | 95 | | 0.4208 | 0.2104 |
| phorate | 91.7 | 0.8721 | 0.4360 | 0.2180 |
| terbufos | 100 | | 0.3990 | 0.1999 |

Each insecticide, with the exception of phorate, was dissolved in 50 mL of acetone containing 0.5% (v/v) of sorbitan monolaurate. The volume of each was brought to 100 mL with water which also contained 0.5% sorbitan monolaurate. Phorate was dissolved in 10 mL of acetone and the volume brought to 100 mL with water. As in Test 1 above, both the acetone and the water contained 0.5% sorbitan monolaurate.

An appropriate number of the fiber flats described above were filled to a depth of 6.5 cm with a sterilized sandy loam soil. The flats were sprayed with the lowest rate of application of insecticide using a machine sprayer calibrated to deliver 30 gallons/acre at 40 pounds/sq. in. with the spray head adjusted to 27 cm above the soil surface. The soil in each flat sprayed with insecticide was combined in a cement mixer and thoroughly mixed. Upon completion of mixing, a 100 mL sample of the soil was saved for use as a seed topping. The remainder of the soil was again placed in the fiber flats in which it had been sprayed. The process was repeated until all the rates of application of the insecticide were soil incorporated.

The soil in the flats was leveled and impressed with a template that provided four evenly spaced furrows in each flat that were 13 cm long and 0.5 cm deep. Seeds of the cottom (*Gossypium hirsutum*) hybrids Paymaster 145 and DPL50, winter wheat (*Triticum aestivum*) Batum hybrid, and velvetleaf (*Abutilon theophrasti*) were each placed in the furrows of the soil of one flat and seeds of corn (*Zea mays*) hybrids PN 3906 and PN 3377, spring wheat hybrid Wheaton, and cotton hybrid Stoneville 825 were each placed in the furrows of the soil of another flat. The four row template was again employed to firmly press the seeds into place. The corresponding 100 mL sample of soil described above was placed uniformly on top of each flat to a depth of approximately 0.5 cm. The flats so treated with insecticides and planted with seeds were placed in a greenhouse for 18 hours prior to spraying the soil surface with clomazone.

Aliquots of a 4.0 pound/gallon emulsifiable concentrate (4.0 EC) formulation of clomazone were weighed into the appropriate containers to provide the rates of application of clomazone as indicated below:

| Application Rate of Clomazone | Weight in Grams of 4.0 EC Formulation of Clomazone Needed |
|---|---|
| 1.0 kg/ha | 1.20 |
| 0.5 | 0.60 |
| 0.25 | 0.30 |
| 0.125 | 0.15 |
| 0.063 | 0.075 |

Each aliquot was dissolved in 160 mL of distilled water. Clomazone at the rates of application indicated was sprayed onto the surface of the soil in the appropriate flats under the same conditions as described above for the spraying of the insecticide solutions. Upon completion of the applications of clomazone the test flats were placed in a greenhouse where they were maintained for 14 days. Untreated control flats and flats treated with clomazone only were included in this test for comparison purposes.

Following the 14-day exposure period each flat was evaluated for percent injury as compared to the untreated control. Percent reduction of injury to the test plants by treatment with insecticide for each rate of application of clomazone was calculated using the formula described in Test 1(A) above.

As shown in Table 3 appended, terbufos, disulfoton, and phorate all reduced clomazone injury to cotton and wheat at the clomazone rate of application of 0.25 kg/ha. Some reduction of clomazone injury was observed on corn and wheat by applications of terbufos, disulfoton and phorate but only at rates of application of clomazone that usually give poor weed control. However, terbufos, disulfoton and phorate would be useful as a safener against the phytotoxic effects of clomazone on wheat or corn in situations where clomazone carryover from one year to the next might be a problem.

3. Tolerance to Clomazone of Certain Crops Treated with Phorate

A. Postemergence and Preemergence Tank mix Application Test

For the postemergence portion of the test, six disposable fiber flats (25 cm×15 cm×8 cm) for each rate of application of clomazone were prepared for seed planting as described in Test 1A above. Two flats for each rate of application of clomazone were required, each containing five different test plants. The test was conducted in triplicate. For each rate of application of clomazone one flat was planted with seeds of the spring wheat (*Triticum aestivum*) hybrid Wheaton, sorghum (*Sorghum vulgare*), corn (*Zea mays*) hybrid PN 3906, sugar beet (*Beta vulgaris*), and cotton (*Gossypium hirsutum*) hybrid DPL50. The other flat was planted with the seeds of rice (*Oryza sativa*) hybrid Mars, corn hybrid PN 3377, sunflower (*Helianthus annua*), winter wheat hybrid Batum, and peanut (*Arachis hypogaea*) hybrid Pronto. The flats were placed in a greenhouse where they were maintained for 7–8 days while the seeds germinated prior to spraying.

Six disposable fiber flats for each rate of application of clomazone for the preemergence portion of the test were planted with the same plant species and in the same manner as described in Test 1B above.

Sufficient amounts of stock test solutions of clomazone and phorate were prepared so that both the postemergence and preemergence portions of the test could be sprayed at one time. Thus, 0.5712 gram of technical clomazone was weighed into an appropriate container and dissolved in 80 mL of 1:1 acetone and water containing 0.5% (v/v) sorbitan monolaurate. A similar stock solution was prepared by dissolving 1.09 grams of 91.7% pure technical phorate in 140 mL of 1:1 acetone and water containing 0.5% sorbitan monolaurate. For the postemergence portion of the test a 20 mL aliquot of the clomazone solution was divided into two 10 mL samples. One 10 mL sample was set aside and the volume of the second 10 mL sample was brought to 20 mL with 1:1 acetone and water as previously described. This solution was also divided into two 10 mL samples. One 10 mL sample was set aside for use as the 0.5 kg/ha rate of application of clomazone. The volume of the second 10 mL sample was brought to 20 mL with additional 1:1 acetone and water. The serial dilution was continued, to provide eight 10 mL solutions of clomazone of diminishing concentration. Each clomazone solution was serially diluted to 20 mL with 10 mL of the stock solution of phorate to provide spray solutions of phorate at an application of 1.0 kg/ha in combination with clomazone at the application rates of 0.5, 0.25, 0.125, 0.0625, 0.0313, 0.0156, 0.0078, and 0.0039 kg/ha.

Spray solutions for the preemergence portion of the test were prepared in the same manner from the stock solutions of clomazone and phorate to provide an application rate of phorate of 1.0 kg/ha in combination with clomazone at the application rates indicated in Table 3 appended.

Spray solutions of clomazone alone were also prepared in the same manner from the stock solution of clomazone for use in both the postemergence and preemergence portions of this test. The rates of application of clomazone alone were the same as the rates of application of clomazone in combination with phorate in the postemergence and preemergence tests. A second stock solution of phorate was prepared by dissolving 0.585 gram of phorate in 150 mL of 1:1 acetone:water containing 0.5% sorbitan monolaurate, for use as spray solutions of phorate alone.

The fiber flats containing test plants for the postemergence test and the flats containing planted seeds for the preemergence test were sprayed with the control and clomazone/phorate test solutions via a machine sprayer calibrated as described in Test 1A above.

Upon completion of the application of the test chemicals the flats were taken to a greenhouse where they were maintained for periods of 11 days and 15 days for the postemergence and preemergence tests, respectively. After these times each test was evaluated for percent injury to the test plants. The data gathered was then used to determine the percent reduction of injury to the crops by using phorate in conjunction with clomazone. The formula for calculating percent reduction of injury is described in Test 1A above. Postemergence and preemergence test results are reported in appended Tables 4 and 5, respectively.

B. Sequential Application Test

This test was conducted in a manner analogous to that previously described in Test 3A above, using the same crop species. Phorate was incorporated into the soil at an application rate of 1.0 kg/ha using the method described in Test 2 above. The phorate spray solution for this test was drawn from the second stock solution prepared for use in Test 3A. After incorporation of the phorate into the soil and the planting of the seeds, the flats were maintained in a greenhouse for 24 hours prior to spraying with clomazone. The clomazone spray solutions were prepared by the serial dilution of a stock solution of 0.1429 gram of technical clomazone in 40 mL of 1:1 acetone:water containing 0.5% sorbitan monolaurate. The rates of application of clomazone were 1.0, 0.5, 0.25, 0.125, and 0.0625 kg/ha. Clomazone and phorate were also applied alone in this test. Untreated controls were also included. Upon completion of applications of test chemicals the flats were returned to the greenhouse where they were maintained for 14 days prior to evaluation of the test. The percent reduction of injury was calculated as previously described in Test 1A.

As shown in Table 6 appended, both preemergence tests, i.e., the tank mix application and the sequential application of phorate with clomazone, resulted in reduction of crop injury when compared to clomazone alone on cotton and winter wheat. Smaller reductions of injury were observed on sunflower and sugar beet. Injury reduction ranged from 33% to 100% on cotton, up to 49% on spring wheat, and up to 78% on winter wheat.

The preemergence tank mix application of phorate with clomazone was less effective than the sequential applications of these products. The tank mix applications best reduced injury on cotton and winter wheat, whereas the sequential applications were also effective on spring wheat.

The postemergence tank mix applications of phorate with clomazone appeared to be the most efficacious of the three methods of application tested. Injury was reduced on spring and winter wheat, sugar beet, cotton and sunflower.

C. Seed Treatment Test

Sufficient amounts of the seeds identified below were weighed into 16 ounce screw-capped glass jars. Weighed also was sufficient 1% wettable powder (1% WP) formulation of phorate to coat the seeds at a rate of application of 0.01 (wt/wt), 0.05 and 0.1% of active ingredient.

| Crop Species | Weight of Seed per Phorate Treatment | Weight of Phorate 1% WP needed per treatment | | |
|---|---|---|---|---|
| | | 0.1% | 0.05% | 0.01% |
| Winter wheat - Batum | 28.4 g | 0.284 g | 0.142 g | 0.070 g |
| Cotton DPL 50 | 16.0 | 0.160 | 0.080 | 0.040 |
| Corn PN 3906 | 19.8 | 0.198 | 0.099 | 0.050 |
| Spring wheat - Wheaton | 15.3 | 0.153 | 0.077 | 0.038 |
| Cotton STV 825 | 18.0 | 0.180 | 0.090 | 0.045 |

In each jar containing seeds was placed 2 mL of an aqueous 2% (wt/wt) solution of the sticker carboxymethylcellulose. The jars were capped and rolled on their sides on a machine with rubber rollers until dispersion of the sticker was complete. The jars were opened and the appropriate amount of phorate as indicated above was added to each jar. The jars were recapped and rolled on their sides until the seeds were uniformly coated with phorate.

Clomazone, 0.6 gram of a 4.0 pound/gallon emulsifiable concentrate (4 EC), was weighed into the appropriate container and dissolved in 40 mL of distilled water. The clomazone solution was serially diluted as described in Test 3A to provide application rates of 1.0, 0.5, 0.25, 0.125 and 0.0625 kg/ha.

Using methods analogous to those previously described, each rate of application of clomazone was sprayed onto the surface of soil contained in an appropriate number of fiber flats. For each rate of application the clomazone was incorporated into the soil of each flat by mixing the soil in a cement mixer, then returning the soil to the flats from which it came. The seeds treated with phorate were planted and the flats placed in a greenhouse where they were maintained for 14 days until evaluation of the test. The test was conducted in triplicate. The test also included untreated seeds in clomazone treated soil, seeds treated with phorate in untreated soil, and untreated seeds in untreated soil. The percent reduction of injury by using phorate in conjunction with clomazone was calculated using the formula described in Test 1A.

As shown in Table 7 appended, cotton was safened to the greatest extent by seed treatments of phorate. At the use rates of clomazone (0.125–0.250 kg/ha), phorate reduced cotton injury by 85 to 100%. Injury at the higher rates of application of clomazone was reduced by 50 to 60%.

Clomazone injury to wheat was reduced generally by 20 to 50% at the clomazone rates of application of 0.0625 to 0.25 kg/ha when the seeds were treated with phorate. Injury reduction to wheat at the highest rate of application of clomazone was 3 to 17%.

Corn injury was reduced by the phorate seed treatment from 20 to 50% at the clomazone rates of application of 0.125 to 0.5 kg/ha. The improved safening of corn to clomazone by the use of a phorate seed treatment as compared to the tank mix applications of phorate suggests that the phorate must be in closer proximity to the seeds for efficacy on corn.

The amount of phorate applied to the seeds did not appear to affect the reduction of clomasone injury to any great extent. The 1.0 g/kg of seed weight application of phorate seemed to reduce injury to the greatest extent on the cotton and wheat cultivars tested.

TABLE 1

Percent Reduction of Injury from Clomazone in Cereal Crops Treated with Certain Insecticides
Postemergence Test

| Insecticide | Insecticide Application Rate | Clomazone Rate of Application | Percent Reduction of Injury* | | | | |
|---|---|---|---|---|---|---|---|
| | | | Spring Wheat | Winter Wheat | Barley | Corn | Sorghum |
| DIMETHOATE | 0.84 (kg/ha) | 16 (g/ha) | 100 | 100 | — | 100 | 54 |
| | | 31 | 88 | 66 | 100 | 100 | −20 |
| | | 63 | 35 | 25 | 30 | 8 | −20 |
| | | 125 | 25 | 23 | 10 | 14 | 30 |
| | | 250 | 8 | −12 | −3 | −8 | −12 |
| DEMETON | 0.28 | 16 | 100 | 65 | — | 100 | 38 |
| | | 31 | 100 | 66 | 83 | 73 | 13 |
| | | 63 | 42 | 28 | 55 | 36 | −12 |
| | | 125 | 15 | 15 | 27 | 20 | 30 |
| | | 250 | 8 | 8 | 0 | 0 | 14 |
| DISULFOTON | 1.12 | 16 | 100 | 100 | — | 100 | 100 |
| | | 31 | 96 | 87 | 100 | 67 | 33 |
| | | 63 | 70 | 66 | 97 | 44 | 20 |
| | | 125 | 53 | 54 | 79 | 34 | 34 |
| | | 250 | 21 | 18 | 40 | 3 | 0 |
| TERBUFOS | 1.12 | 16 | 100 | 100 | — | 100 | 0 |
| | | 31 | 100 | 100 | 100 | 80 | 23 |
| | | 63 | 91 | 81 | 100 | 60 | 0 |
| | | 125 | 75 | 49 | 79 | 40 | 20 |
| | | 250 | 25 | 18 | 31 | 0 | 0 |
| PHORATE | 1.0 (kg/ha) | 16 (g/ha) | 100 | 100 | — | 100 | 38 |
| | | 31 | 96 | 100 | 100 | 100 | 33 |
| | | 63 | 93 | 81 | 91 | 80 | 0 |
| | | 125 | 43 | 49 | 79 | 50 | 30 |
| | | 250 | 29 | 11 | 34 | 0 | 9 |

Numbers preceded by a minus sign indicate more injury was observed in the crops treated with insecticide than was observed in the crops not treated with insecticide.
*Average of four replicates. Injury indicated by discoloration or chlorosis.

TABLE 2

Preemergence Test
Percent Reduction of Injury from Clomazone in Cereal Crops by Treatment with Certain Insecticides

| Insecticide | Insecticide Application Rate | Clomazone Rate of Application | Percent Reduction of Injury* | | | | |
|---|---|---|---|---|---|---|---|
| | | | Spring Wheat | Winter Wheat | Barley | Corn | Sorghum |
| DIMETHOATE | 0.84 (kg/ha) | 16 (g/ha) | 50 | 71 | 100 | 17 | 11 |
| | | 31 | 39 | 56 | 78 | −9 | 0 |
| | | 63 | 10 | 25 | 13 | 19 | 0 |
| | | 125 | 10 | −15 | 9 | 6 | −10 |
| | | 250 | 3 | −17 | 5 | −5 | −28 |
| DEMETON | 0.28 | 16 | 46 | 66 | 100 | 100 | 36 |
| | | 31 | −15 | 16 | 17 | 13 | 15 |
| | | 63 | 0 | 17 | 13 | 7 | −8 |
| | | 125 | −10 | −15 | 15 | 0 | −10 |
| | | 250 | 0 | −14 | 0 | −5 | −19 |
| DISULFOTON | 1.12 | 16 | 64 | 100 | 100 | 50 | 11 |
| | | 31 | 24 | 60 | 83 | 35 | −15 |
| | | 63 | 27 | 33 | 39 | 30 | 0 |
| | | 125 | 0 | 4 | 34 | 9 | −16 |
| | | 250 | 3 | −3 | 16 | 0 | −9 |

TABLE 2-continued

Preemergence Test
Percent Reduction of Injury from Clomazone in Cereal Crops
by Treatment with Certain Insecticides

| Insecticide | Insecticide Application Rate | Clomazone Rate of Application | Percent Reduction of Injury* | | | | |
|---|---|---|---|---|---|---|---|
| | | | Spring Wheat | Winter Wheat | Barley | Corn | Sorghum |
| TERBUFOS | 1.12 | 16 | 100 | 100 | 100 | 100 | 71 |
| | | 31 | 70 | 78 | 100 | 43 | 39 |
| | | 63 | 31 | 45 | 66 | 30 | 5 |
| | | 125 | 24 | 9 | 38 | 9 | 10 |
| | | 250 | 17 | −3 | 21 | 0 | 6 |
| PHORATE | 1.0 (kg/ha) | 16 (g/ha) | 100 | 100 | 100 | 100 | 54 |
| | | 31 | 61 | 78 | 100 | 43 | 15 |
| | | 63 | 48 | 42 | 74 | 30 | 0 |
| | | 125 | 10 | 4 | 47 | 15 | 10 |
| | | 250 | 17 | −3 | 21 | −8 | −9 |

Numbers preceded by a minus sign indicate more injury was observed in the crops treated with insecticide than was observed in the crops not treated with insecticide.
*Average of four replicates. Injury indicated by discoloration or chlorosis.

TABLE 3

Percent Reduction of Injury from Clomazone in Cotton and Cereal Crops
Treated with Certain Insecticides
Pre-Plant Incroporated Test.

| Clomazone Application Rate | Insecticide | Insecticide Application Rate | Percent Reduction of Injury* | | | | | | | |
|---|---|---|---|---|---|---|---|---|---|---|
| | | | Cotton Paymaster 145 | Cotton DPL50 | Cotton STV825 | Winter Wheat | Spring Wheat | Corn PN3377 | Corn PN3906 | Velvet-Leaf |
| 0.0625 kg/ha | DISULFOTON | 0.56 kg/ha | 100 | 100 | 87 | −9 | −33 | −13 | 100 | −9 |
| | | 1.12 | 94 | 100 | 87 | 14 | −25 | −66 | 62 | −49 |
| 0.125 | | 0.56 | 82 | 100 | 67 | 13 | −20 | −14 | 15 | −4 |
| | | 1.12 | 93 | 100 | 83 | 44 | −14 | −13 | 44 | 9 |
| 0.25 | | 0.56 | 68 | 65 | 54 | 3 | −19 | −21 | −19 | 1 |
| | | 1.12 | 75 | 65 | 46 | 19 | −4 | −21 | −4 | 17 |
| 0.5 | | 0.56 | 67 | 68 | 37 | 7 | −3 | −8 | −12 | 0 |
| | | 1.12 | 78 | 73 | 43 | 2 | −9 | −5 | −6 | 0 |
| 1.0 | | 0.56 | 56 | 56 | 7 | 2 | −2 | 0 | −2 | 0 |
| | | 1.12 | 67 | 63 | 28 | 2 | 0 | 0 | −2 | 0 |
| 0.0625 | PHORATE | 0.56 | 100 | 100 | 53 | 60 | 8 | −13 | 100 | −23 |
| | | 1.12 | 100 | −50 | 100 | 30 | 25 | −43 | 100 | −28 |
| | | 2.24 | 100 | −50 | 87 | 65 | 18 | −70 | −108 | −26 |
| 0.125 | | 0.56 | 89 | 100 | 73 | 25 | 14 | −30 | 15 | 6 |
| | | 1.12 | 89 | 100 | 93 | 18 | 6 | −14 | 63 | 0 |
| | | 2.24 | 100 | 100 | 93 | 70 | 34 | −10 | 82 | 11 |
| 0.25 | | 0.56 | 70 | 40 | 60 | 21 | −17 | −11 | 19 | 0 |
| | | 1.12 | 80 | 65 | 68 | 19 | 3 | −18 | 29 | −4 |
| | | 2.24 | 100 | 75 | 81 | 37 | 14 | −18 | 4 | −4 |
| 0.5 | | 0.56 | 73 | 76 | 37 | 8 | 19 | −5 | −6 | 2 |
| | | 1.12 | 72 | 81 | 56 | 5 | 8 | −8 | −6 | 0 |
| | | 2.24 | 92 | 89 | 53 | 20 | 8 | −8 | 6 | 0 |
| 1.0 | | 0.56 | 41 | 67 | 15 | 0 | −2 | 0 | −2 | 0 |
| | | 1.12 | 66 | 72 | 41 | 3 | −2 | 0 | −2 | 0 |
| | | 2.24 | 69 | 81 | 56 | 0 | −2 | 0 | 1 | 0 |
| 0.0625 | TERBUFOS | 0.56 | 91 | 100 | 80 | 47 | 25 | −34 | 100 | 0 |
| | | 1.12 | 79 | 100 | 67 | 58 | 0 | −49 | 85 | −18 |
| 0.125 | | 0.56 | 44 | 75 | 60 | 48 | 14 | −7 | 89 | 3 |
| | | 1.12 | 70 | 75 | 77 | 52 | −20 | −8 | 100 | 14 |
| 0.25 | | 0.56 | 55 | 60 | 46 | 13 | 19 | −18 | 24 | 1 |
| | | 1.12 | 70 | 35 | 59 | 21 | −4 | −21 | 4 | −5 |
| 0.5 | | 0.56 | 43 | 60 | 37 | 3 | −3 | −8 | −5 | 2 |
| | | 1.12 | 36 | 57 | 24 | 13 | −3 | −8 | 4 | 3 |
| 1.0 | | 0.56 | 9 | 26 | 12 | 0 | −2 | 0 | −2 | 0 |
| | | 1.12 | 40 | 26 | 5 | 2 | 0 | 2 | 0 | 0 |

The negative numbers indicate more injury (from insecticide) than when no insecticide applied.
*Average of four replicates. Injury indicated by discoloration or chlorosis.

TABLE 4

Percent Reduction in Injury from Clomazone in Certain Crops
Treated with Phorate at 1.0 kg/ha
Sprayed Tank Mix Test - Postemergence

| Clomazone Application Rate | Percent Reduction of Injury* | | | | | | | | | |
|---|---|---|---|---|---|---|---|---|---|---|
| | Cotton | Winter Wheat | Spring Wheat | Corn PN3377 | Corn PN3906 | Rice | Sunflower | Peanut | Sorghum | Sugar Beet |
| 0.0039 kg/ha | 100 | 100 | 100 | 100 | 100 | A | 41 | — | 100 | 100 |
| 0.0078 | 100 | 95 | 91 | 100 | A | A | 16 | — | 50 | 100 |
| 0.0156 | 100 | 93 | 93 | A | −60 | A | 19 | — | 60 | 94 |

TABLE 4-continued
Percent Reduction in Injury from Clomazone in Certain Crops
Treated with Phorate at 1.0 kg/ha
Sprayed Tank Mix Test - Postemergence

| Clomazone Application Rate | Percent Reduction of Injury* | | | | | | | | | |
|---|---|---|---|---|---|---|---|---|---|---|
| | Cotton | Winter Wheat | Spring Wheat | Corn PN3377 | Corn PN3906 | Rice | Sunflower | Peanut | Sorghum | Sugar Beet |
| 0.0313 | 70 | 74 | 92 | A | −467 | A | 6 | — | 57 | 84 |
| 0.0625 | 56 | 35 | 43 | 52 | −153 | A | 14 | — | 25 | −10 |
| 0.125 | 48 | 30 | 26 | 33 | −16 | 70 | 14 | — | 11 | 21 |
| 0.25 | 33 | 28 | 15 | −28 | −9 | 11 | 4 | 40 | −6 | 15 |
| 0.5 | 21 | 13 | 0 | 0 | −26 | 6 | 5 | 14 | 0 | 7 |

A - Clomazone alone at these rates of application did not injure the crops.
The negative numbers indicate more injury (from insecticide) than when no insecticide applied.
*Average of four replicates. Injury indicated by discoloration or chlorosis.

TABLE 5
Percent Reduction of Injury from Clomazone in Certain Crops
Treated with Phorate at 1.0 kg/ha
Sprayed Tank Mix Test - Preemergence

| Clomazone Application Rate | Percent Reduction of Injury* | | | | | | | | | |
|---|---|---|---|---|---|---|---|---|---|---|
| | Cotton | Winter Wheat | Spring Wheat | Corn PN3377 | Corn PN3906 | Rice | Sunflower | Peanut | Sorghum | Sugar Beet |
| 0.0625 kg/ha | 33 | 14 | 27 | 10 | 100 | A | 20 | A | −85 | −86 |
| 0.125 | 71 | 19 | −8 | −38 | 30 | 43 | −6 | — | −8 | 26 |
| 0.25 | 82 | 10 | 4 | −3 | 6 | 45 | 0 | — | 14 | 48 |
| 0.5 | 64 | 3 | 5 | 11 | −2 | 6 | 6 | 100 | 5 | 25 |
| 1.0 | 41 | −2 | 11 | 0 | −12 | 15 | −2 | −100 | 1 | 23 |

A - Clomazone alone at these rates of application did not injure the crops.
The negative numbers indicate more injury (from insecticide) than when no insecticide applied.
*Average of four replicates. Injury indicated by discoloration or chlorosis.

TABLE 6
Percent Reduction of Injury from Clomazone in Certain Crops
Treated with Phorate Pre-Plant Incorporated at 1.0 kg/ha
Sequential Application Test

| Clomazone Application Rate | Percent Reduction of Injury* | | | | | | | | | |
|---|---|---|---|---|---|---|---|---|---|---|
| | Cotton | Winter Wheat | Spring Wheat | Corn PN3377 | Corn PN3906 | Rice | Sunflower | Peanut | Sorghum | Sugar Beet |
| 0.0625 kg/ha | 100 | 76 | 46 | 0 | 100 | A | 60 | A | −50 | −86 |
| 0.125 | 100 | 55 | 8 | 0 | −130 | 26 | 37 | — | −18 | 0 |
| 0.25 | 100 | 31 | 49 | 0 | −106 | 45 | 15 | 100 | 21 | 18 |
| 0.5 | 93 | 20 | 34 | −2 | 37 | 10 | 11 | 100 | 13 | 0 |
| 1.0 | 63 | 10 | 29 | 0 | 0 | 10 | 2 | — | 0 | 27 |

A - Clomazone alone at these rates of application did not injure the crops.
The negative numbers indicate more injury (from insecticide) than when no insecticide applied.
*Average of four replicates. Injury indicated by discoloration or chlorosis.

TABLE 7
Percent Reduction of Injury from Clomazone in Certain Crops
Treated with Phorate
Seed Treatment Test

| Clomazone Application Rate | Phorate Application Rate | Percent Reduction of Injury* | | | | |
|---|---|---|---|---|---|---|
| | | Cotton DPL50 | Cotton STV825 | Wheat Batum | Wheat Wheaton | Corn |
| 0.0625 kg/ha | 0.1 g/kg seed | 100 | 63 | 51 | 26 | A |
| | 0.5 | 100 | 75 | 43 | 34 | A |
| | 1 | 100 | 75 | 55 | 54 | |
| 0.125 | 0.1 | 100 | 93 | 28 | 25 | 81 |
| | 0.5 | 100 | 88 | 25 | 25 | 54 |
| | 1 | 100 | 95 | 25 | 25 | 38 |
| 0.25 | 0.1 | 95 | 84 | 13 | 2 | 35 |
| | 0.5 | 100 | 90 | 15 | 20 | 35 |
| | 1 | 100 | 91 | 20 | 18 | 35 |
| 0.5 | 0.1 | 50 | 47 | 8 | 3 | 20 |
| | 0.5 | 50 | 47 | 7 | 3 | 21 |
| | 1 | 63 | 63 | 17 | 6 | 21 |
| 1.0 | 0.1 | 44 | 37 | 5 | −3 | 8 |
| | 0.5 | 40 | 40 | 3 | 0 | 5 |
| | 1 | 58 | 47 | 5 | 0 | 10 |

A - Clomazone at this low rate of application did not injure the crops
The negative numbers indicate more injury (from insecticide) than when no insecticide applied.
*Average of four replicates. Injury indicated by discoloration or chlorosis.

I claim:

1. A method of controlling undesirable vegetation in the locus of a crop, which comprises applying to the locus thereof in the presence of an agriculturally acceptable carrier a herbicidally effective amount of clomazone and, as an antidote to clomazone, a safening amount of at least one organophosphorus compound of the formula

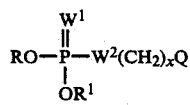

wherein $W^1$ and $W^2$ independently are oxygen or sulfur, x is an integer of from 1 to 4, Q is $SR^2$ or and R, $R^1$, $R^2$ and $R^3$ are alkyl($C_1$-$C_{13}$), provided that both $W^1$ and $W^2$ are not oxygen.

2. The method of claim 1 wherein x of the formula is 1 or 2, Q is $SR^2$ and R, $R^1$ and $R^2$ independently contain 1 to 6 carbon atoms.

3. The method of claim 1 wherein x of the formula is 1 or 2, Q is

and R, $R^1$ and $R^3$ independently contain 1 to 6 carbon atoms.

4. The method of claim 1 wherein the organophosphorus compound is phorate.

5. The method of claim 1 wherein the organophosphorus compound is disulfoton.

6. The method of claim 1 wherein the organophosphorus compound is terbufos.

7. The method of claim 1 wherein the organophosphorus compound is demeton.

8. The method of claim 1 wherein the organophosphorus compound is dimethoate.

9. The method of claim 1 wherein the crop is cotton.

10. themethod of claim 4 wherein the crop is cotton.

11. The method of claim 5 wherein the crop is cotton.

12. The method of claim 6 wherein the crop is cotton.

13. The method of claim 7 wherein the crop is cotton.

14. The method of claim 8 wherein the crop is cotton.

15. The method of claim 1 wherein the crop is a cereal crop.

16. The method of claim 15 wherein the cereal is a small grain cereal.

17. The method of claim 1 wherein the crop is corn.

18. The method of claim 1 wherein the organophosphorus compound is applied prior to application of the clomazone.

19. The method of claim 1 wherein the organophosphorus compound is applied to seeds of the crop followed by application of clomazone to the soil in which the seeds are planted or are to be planted.

20. The method of claim 1 wherein the organophosphorus compound is applied to the soil prior to planting of the crop, and the clomazone is applied to the soil after planting.

21. The method of claim 1 wherein the clomazone and organophosphorus compound are applied in admixture.

22. The method of claim 1 wherein the ratio of organophosphorus compound to clomazone is at least about 2:1 by weight.

23. The method of claim 1 wherein the ratio of the organophosphorus compound to clomazone is from about 2:1 to about 10:1 by weight.

24. A herbicidal composition for control of undesirable vegetation in the locus of a crop, comprising a herbicidally effective amount of clomazone and a safening amount of an organophosphorus compound of the formula

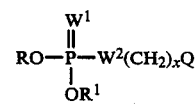

wherein $W^1$ and $W^2$ independently are oxygen or sulfur, x is an integer of from 1 to 4, Q is $SR^2$ or

and R, $R^1$, $R^2$ and $R^3$ are alkyl ($C_1$–$C_{13}$), provided that both $W^1$ and $W^2$ are not oxygen.

25. The composition of claim 24 wherein x of the formula is 1 or 2, Q is $SR^2$, and R, $R^1$ and $R^2$ independently contain 1 to 6 carbon atoms.

26. The composition of claim 24 wherein x of the formula is 1 or 2, Q is

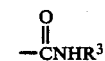

and R, $R^1$ and $R^3$ independently contain 1 to 6 carbon atoms.

27. The composition of claim 24 wherein the ratio of organophosphorus compound to clomazone is at least about 2:1 by weight.

28. The composition of claim 24 wherein the ratio of organophosphorus compound to clomazone is from about 2:1 to about 10:1 by weight.

29. The composition of claim 24 wherein the organophosphorus compound is phorate.

30. The composition of claim 24 wherein the organophosphorus compound is disulfoton.

31. The composition of claim 24 wherein the organophosphorus compound is terbufos.

32. The composition of claim 24 wherein the organophosphorus compound is demeton.

33. The composition of claim 24 wherein the organophosphorus compound is dimethoate.

* * * * *